United States Patent [19]

Kirmann

[11] Patent Number: Plant 6,020

[45] Date of Patent: Sep. 22, 1987

[54] GERANIUM PLANT NAMED PEGGY

[75] Inventor: Wolfgang Kirmann, Langenzersdorf, Austria

[73] Assignee: Mirko Vavra, Bisamberg, Austria

[21] Appl. No.: 811,117

[22] Filed: Dec. 19, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Peggy having light red-purple flower color, variegated with dark red-purple; very early flowering; good bud production at night temperatures up to 16° C., thus providing a long and continuous flowering period; compact, self-branching growth habit; very floriferous habit; and ease of propagation and good rooting habit.

2 Drawing Figures

The present invention comprises a new and distinct cultivar of geranium, botanically known as *Pelargonium domesticum,* and hereinafter referred to by the cultivar name Peggy.

Peggy is a product of a planned breeding program which had the objective of creating new geranium cultivars having a compact growth habit, early flowering and long flowering period, good flower production, relatively small foliage and light purple flower color.

Peggy was originated from a hybridization made by applicant in a controlled breeding program in Bisamberg, Austria in 1978. The female parent was Jupiter 75, a cultivar characterized by its tall growth habit, large lilac flowers with red stripes and very early flowering. The male parent of Peggy was a cultivar designated as seedling 708/76 having a compact growth habit, broad, dark green foliage and relatively small violet petals.

Peggy was discovered and selected as one flowering plant within the progeny of the stated cross by applicant on Feb. 25, 1979 in a controlled environment in Bisamberg, Austria.

The first act of asexual reproduction of Peggy was accomplished when vegetative cuttings were taken from the initial selection on Aug. 20, 1979 in a controlled environment in Bisamberg, Austria by a technician working under formulations established and supervised by Wolfgang Kirmann. Horticultural examination of selected units initiated in the spring of 1980 has demonstrated that the combination of characteristics as herein disclosed for Peggy are firmly fixed and are retained through successive generations of asexual reproduction.

Peggy has not been observed under all possible environmental conditions. The phenotype may vary significantly with variations in environment such as temperature, light intensity, and day length. The following observations, measurements and comparisons describe plants grown in Bisamburg, Austria under conditions which approximate those generally used in commercial practice.

The following traits have been repeatedly observed and are determined to be basic characteristics of Peggy, which in combination distinguish this geranium as a new and distinct cultivar.

1. Light red-purple flower color variegated with dark red-purple at the throat of each petal.
2. Very early flowering and long flowering period.

3. Small, medium green foliage.
4. Compact, self-branching growth habit.
5. Good bud production and very floriferous.
6. Propagates well, with very good rooting habit.
7. Buds are produced under normal greenhouse conditions (5000 Lux for 16 hours per day) at 14°-16° C. This is well above the cooler temperatures required for previous *domesticum* varieties. In addition, plants flowered indoors can be transplanted outdoors and will continue blooming at night temperatures as high as 16° C. Known *domesticum* cultivars will produce buds outdoors only at night temperatures of 10° C. or lower.
8. Peggy is unique with regard to the combined features of compactness, continuous flowering, floriferous habit, and light red-purple flower color.

Of the many commercial cultivars known to the present inventor, the most similar in comparison to Peggy is Jubilante, an unpatented but commercial cultivar. In comparison to Jubilante, Peggy has a more compact growth habit, flowers earlier and has better flower production, and has a more intense pink color.

The accompanying photographic drawings show typical flower and foliage characteristics of Peggy with colors being as true as possible with illustrations of this type.

Sheet 1 is a perspective view of a potted plant of Peggy.

Sheet 2 is a black and white print showing the upper surface of immature and mature plants of Peggy.

In the following description color references are made to The Royal Horticultural Society Colour Chart (RHS). The color values were determined at 9:00 a.m. on May 23, 1985 under 35,000 Lux light intensity in a greenhouse at Hillscheid, Federal Republic of Germany.

Classification:

*Botanical.*—*Pelargonium domesticum.*

*Commercial.*—Commonly referred to as a "Martha Washington" geranium, and having the cultivar name Peggy.

INFLORESCENCE

A. Umbel:

*Average diameter.*—Relatively large, 95-120 mm.

*Peduncle length.*—Normal.

*Pedicel length.*—Normal.

B. Corolla:

*Average diameter.*—65–80 mm; floriferousness results in total inflorescence diameter extending approximately to edge of foliage.

*Form.*—Five-six petals; symmetric.

*Color (general tonality from a distance of three meters).* —Light purple with dark red-purple variegation at the approximate center of each petal.

*Color (upper surface).*—73B, variegated with 60A.

C. Bud:

*Shape.*—Elongated.

*Color.*—White with lilac.

D. Reproductive organs:

*Androecium.*—Red-yellow; 7 stamens.

*Gynoecium.*—Five to seven part.

E. Spring flowering response period: Very early.

F. Durability: Good.

PLANT

A. Foliage:

*Form.*—Zygomorphic with a nectar spur.

*Margin.*—Crenate to serrate and sharply indented.

*Color (upper surface).*—Medium green.

*Tolerance of Botrytis and soil fungi.*—Good.

B. General appearance and form:

*Internode length.*—Short.

*Branching pattern.*—Excellent.

*Height.*—Compact.

I claim:

1. A new and distinct cultivar of geranium named Peggy, as described and illustrated, and particularly characterized by its light red-purple flower color, variegated with dark red-purple; very early flowering; good bud production at night temperatures up to 16° C., thus providing a long and continuous flowering period; compact, self-branching growth habit; very floriferous habit; and by its ease of propagation and good rooting habit.

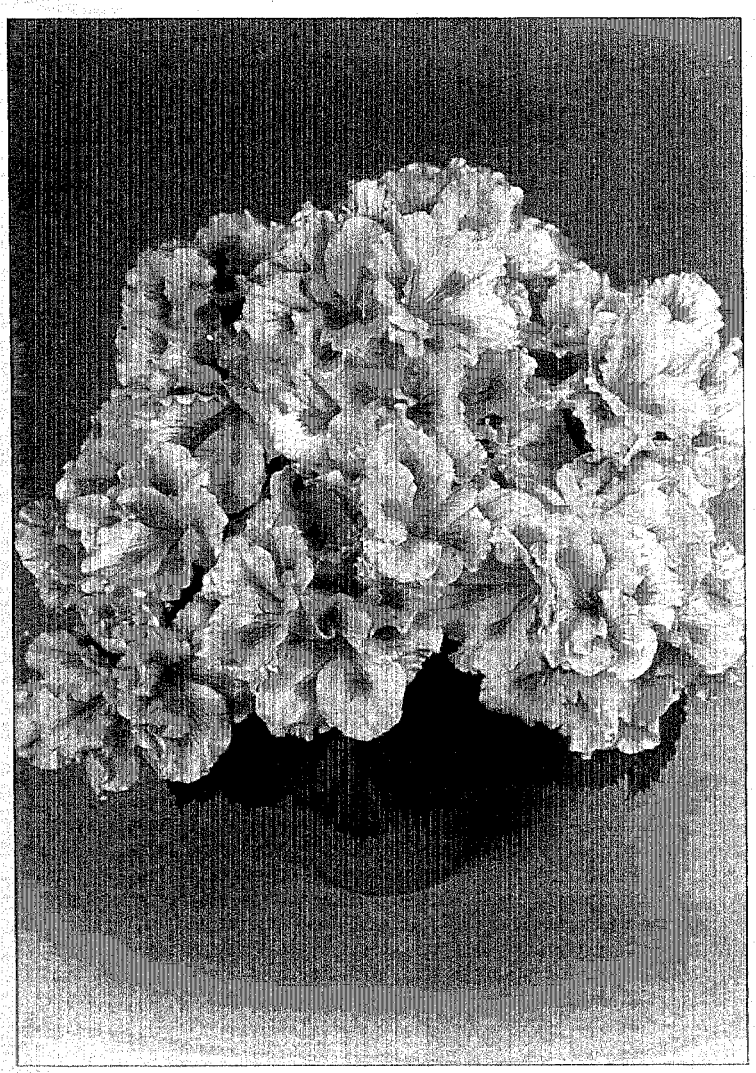

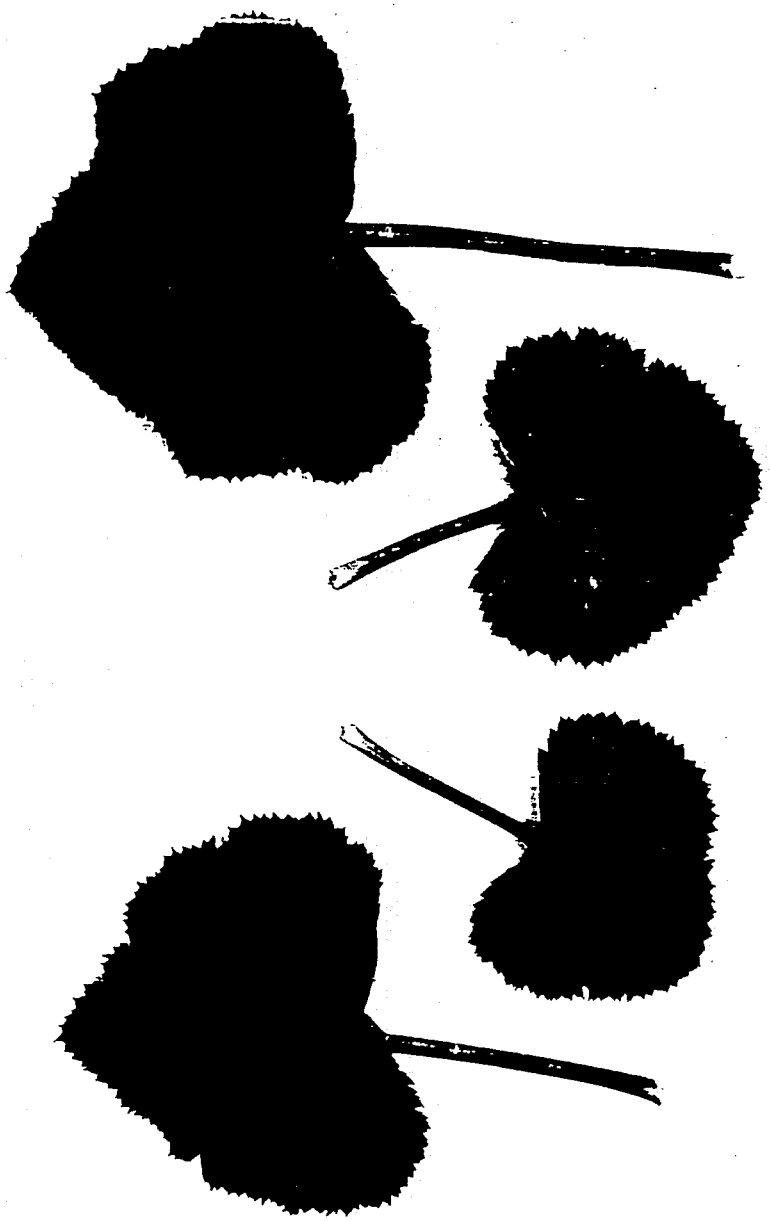

* * * * *